United States Patent [19]

Langer et al.

[11] Patent Number: 4,657,543

[45] Date of Patent: Apr. 14, 1987

[54] ULTRASONICALLY MODULATED POLYMERIC DEVICES FOR DELIVERING COMPOSITIONS

[75] Inventors: Robert S. Langer, Somerville; Joseph Kost, Brookline, both of Mass.

[73] Assignee: Massachusetts Institute of Technology, Cambridge, Mass.

[21] Appl. No.: 633,366

[22] Filed: Jul. 23, 1984

[51] Int. Cl.$^4$ ................................................ A61K 9/22
[52] U.S. Cl. ..................................... 604/891; 604/22; 604/49; 604/290; 128/24 A
[58] Field of Search .............................. 604/890–897, 604/285, 49, 93, 290, 28, 22; 128/24 A, 328, 804; 204/157.15, 157.62

[56] References Cited

U.S. PATENT DOCUMENTS

| | | | |
|---|---|---|---|
| 3,464,413 | 9/1969 | Goldfarb et al. | 604/306 |
| 3,474,777 | 10/1969 | Figge et al. | 604/28 |
| 4,144,317 | 3/1979 | Higuchi et al. | 604/890 |
| 4,182,750 | 1/1980 | Sullivan et al. | 604/28 |
| 4,249,531 | 2/1981 | Heller et al. | 604/891 |
| 4,468,220 | 8/1984 | Willbanks | 604/890 |

OTHER PUBLICATIONS

Blackshear; "Implantable Drug-Delivery Systems"; Scientific America; Dec. 1979; pp. 66–73.

Primary Examiner—Dalton L. Truluck
Assistant Examiner—Mario Costantino
Attorney, Agent, or Firm—Paul J. Cook

[57] ABSTRACT

A composition such as a biologically active substance is delivered upon demand from a polymeric matrix by exposing the polymeric matrix containing the composition to ultrasonic energy.

6 Claims, 5 Drawing Figures

ULTRASONICALLY MODULATED POLYMERIC DEVICES FOR DELIVERING COMPOSITIONS

The government has rights in this invention prusuant to grant Number NIH-5-R01-GM26198-06 awarded by the Department of Health and Human Services.

BACKGROUND OF THE INVENTION

Recently there have been many advances in the development of polymeric systems for delivering drugs. However, nearly all of these systems release drugs at decreasing or, at best, constant rates. Prior to this invention there has been no satisfactory means for increase in the release rates on demand nor has there been any way to control drug administration externally from the body once the release process has commenced from the implanted polymer-drug composition. It has been proposed to magnetically modulate drug delivery from implanted polymer-drug compositions by utilizing a composition that includes small magnetic beads imbedded in the polymer together with the drug. Release rates can be enhanced when desired by a oscillating external magnetic field. However, the extent to which release rates of the drug can be increased by the magnetic field has been unduly limited so that it is difficult to apply such a system to a patient who requires a relatively large dosage of drug within a short period of time.

Constant rate delivery also may not be sufficient to deliver drugs in a way that will closely resemble a homeostatic process. This situation is particularly acute in the case of insulin administration for the diabetic. In diabetes mellitus, augmented insulin delivery is required for short time periods after meal consumption.

Accordingly, it would be highly desirable to provide a means for rapidly delivering drugs in vivo from an implant. It would be desirable to provide such a drug delivery system which is capable of delivering the drug at much higher rates than is available from present drug delivery systems.

SUMMARY OF THE INVENTION

In accordance with this invention, there is provided a process for delivering a composition such as a drug from a polymeric matrix which includes the composition. In one particular aspect of this invention, the composition comprises a drug which is delivered from a polymeric matrix that is implanted in vivo. Delivery of the composition from the polymeric matrix is activated by an external source of ultrasonic energy capable of degrading the polymeric matrix thereby to effect release of the composition incorporated into the polymeric matrix. The polymeric matrix containing the composition to be released is surrounded by a liquid medium such as that is available in vivo and then is subjected to ultra-sound shock wave which accelerates degradation of the polymer and thereby effects release of the composition incorporated in the polymer. The process of this invention is suitable for release of any composition which can be incorporated within a polymeric matrix and subsequently can be released through the liquid medium surrounding the polymeric matrix.

DESCRIPTION OF THE DRAWING

The detailed description of the present invention may be more easily and completely understood when taken in conjunction with the accompanying drawing, in which.

DESCRIPTION OF SPECIFIC EMBODIMENTS

Figure 1:
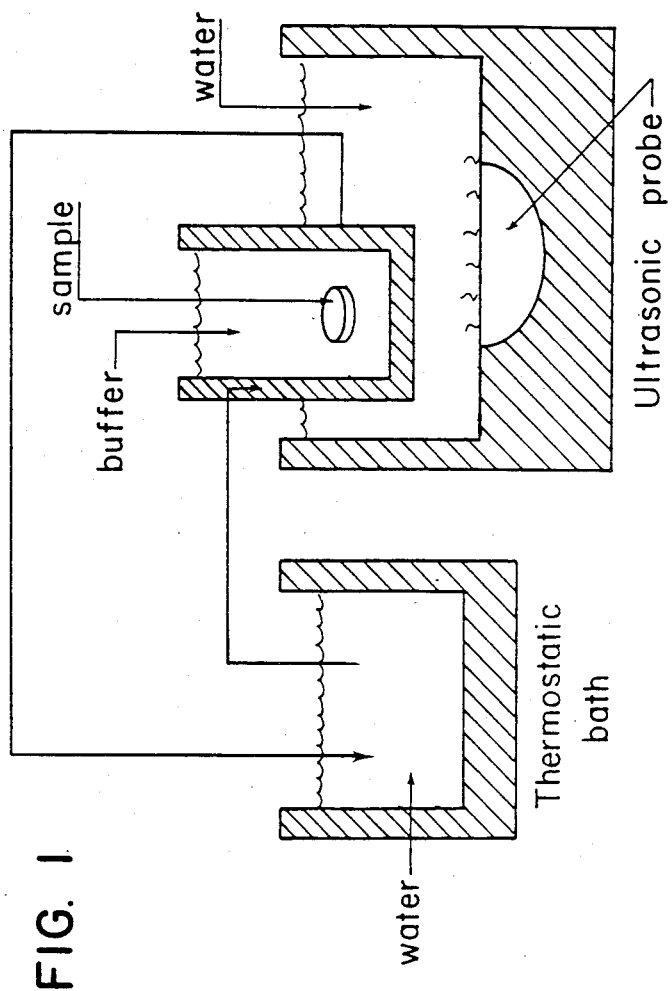
FIG. 1 is a cross-sectional view of a thermostatically controlled ultrasonic bath useful for measuring the increased rate of release of drugs from bioerodible polyanhydride matrices.

In accordance with this invention, a polymeric matrix containing the composition which is desired to be released in a controlled manner is first produced. In the case of the embodiment wherein it is desired to release drugs from the polymeric matrix in vivo, the polymeric matrix is biocompatible. The polymeric matrix is capable of being degraded by ultrasonic energy such that the incorporated composition is released at a rate within a desired release range, or, in the case of nondegradable polymers, release is enhanced presumably due to the effects of cavitation or other mechanical effects.

Representative suitable polymers include polyanhydrides having the formula:

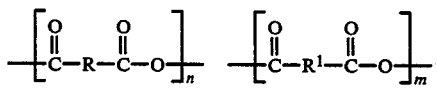

wherein R or R$^1$ is a linking moity having a hydrophobicity such as alkyl group bearing from 1 to 20 carbon atoms, a backbone having aromatic moities such as p-carboxyphenoxy methane, benzyl substituted or unsubstituted benzenes or pyridine or other heterocyclic aromatic or the like. The homopolymer (R=R$^1$) and the copolymer (R≠R$^1$) can have an average degree of polymerization ranging from about 10 to 106. The monomers in the copolymer can be distributed regularly or at random. Since the anhydride linkage is highly reactive active toward hydrolysis, it is preferable that the polymer backbone be hydrophobic in order to attain the heterogeneous erosion of the encapsulated composition. Hydrophobicity can be regulated easily, for example, by regulating the concentration of aromatic moities in the linking backbone, or by monitoring the monomer ratio in the copolymer. A paricularly suitable backbone comprises the acid such as 1-phenylamine, tryptophan, tyrosine or glycine. Other suitable polymers include ethylene-vinyl acetate, polylactic acid, polyglutamic acid, polycaprolactone, lactic/glycolic acid copolymers, polyorthoesters, polyamides or the like. Nondegradable polymers incude ethylene-vinyl acetate, silicone, hydrogels such as polyhydroxyethylmethacrylate, polyvinyl alcohol and the like.

Examples of suitable biologically active substances are interferon, anti-angiogenesis factors, antibodies, antigens, polysaccharides, growth factors, antibodies, antigens, polysaccharides, growth factors, hormones including insulin, glucogen, parathyroid and pituitary hormones, calcitonin, vasopressin renin, prolactin, growth hormones, thyroid stimulating hormone, corticotrophin, follicle stimulating hormone, luteinizing hormone and chorionic gonadotropins; enzymes including soybean, tyrpsin inhibitor, lysozyme, catalase, tumor angiocgenesis factor, cartilage factor, transferases, hydrolases, lysases, isomerases, proteases, ligases and oxidoreductases such as esterases, phosphatases, glysidases, and peptidases; enzyme inhibitors such as leupeptin, antipain, chrymostatin and pepstatin; and drugs such as steroids, anti-cancer drugs or antibiotics. Other representative compositions which can be encapsulated within a polymeric matrix and subsequently released with ultrasonic energy when the polymeric matrix is surrounded by a liquid or a solid medium include aromas such as perfumes, pheromones, insecticides, pesticides or the like.

The relative proportions of the composition to be released to form the two-phased system can be modified over a wide range depending upon the molecule to be administered or the desired effect. Generally, the molecule can be present in an amount which will be released over controlled periods of time, according to predetermined desired rates, which rates are dependent upon the initial concentration of the active molecule in the polymeric matrix and the level of ultrasonic energy to which it is subjected. This necessarily implies a quantity of molecule greater than the standard single dosage. Proportions suitable for the purposes of this invention can range from about 0.01 to 50 parts by weight of the active composition to between about 99.99 and about 50 parts by weight of the polymeric matrix, preferably between about 10 and about 30 parts by weight in the case of the biologically active molecule to be implanted to give 100 parts by weight of the final system.

The polymeric matrix in the composition to be released can be admixed intimately in any convenient manner, preferably by mixing the components a powders and subsequently forming the mixture into a desired shape such as by thermal forming at a temperature less than that which the composition will become degraded and at which the polymer has desired morphological properties. Generally, the final composition is formed as a slab which can be circular, rectangular or the like and having a thickness between about 0.1 mm and about 100 mm in a total surface area between about .0.01 $cm^2$ and about 1,000 $cm^2$ preferably between about 1 $cm^2$ and about 100 $cm^2$ The delivery systems of this invention can be manufactured as devices that can take a wide range of shapes, sizes and forms by delivering the active molecule to different environments of use. For example, the systems can be made as devices including buccal and oral devices; vaginal and intrauterine devices of cylindrical, bullet, elliptical, circular, bulbous, loo, bow or any other shape that lends itself to placement in a particular environment such as an invivo implant. The devices also include ocular devices of any geometric shape for comfortable placement in the cul de sac such as ellipsoid, bean, banana, circular, rectangular, doughnut, crescent and heart-ring shaped devices. In cross section, the ocular devices can be doubly convex, concave, oconcavo-convex and the like. The dimensions of the ocular devices can vary according to the size of the eye, with satisfactory eye devices generally having a length of 4-20 mm or a width of 1-15 mm and a thickness of 0.1-4 mm. Other devices made according to this invention include implants, anal, pessaries and prosthetic devices, artificial glands for dispensing a pharmaceutically active molecular agent having a physiological function essentially equivalent to a corresponding meutral gland, cervical, nasal, ear and skin devices.

The polymeric matrix utilized in the present invention can be manufactured by standard techniques provided as is important to this invention that such manufacture includes process steps such as blending, mixing or the equivalent thereof for structurally defining the system comprising the molecule to be released and the polymeric matrix. For example, one suitable method for making the systems comprises the polymer and an appropriate solvent, thereby to form a casting solution, mixing a known amount of the composition to be released in the casting solution, charging the solution into a mold and then drying the mold, usually under vacuum, causing the polymer to precipitate in forming the matrix with the molecule to be released therein. Alternatively, the polymer in the form of a powder can be admixed with the molecule to be released in the form of a powder and then molded under adequate temperature and pressure to the desired shape, through injection, compression, or extrusion.

After the polymeric matrix containing the composition or molecule to be released is implanted in the desired and liquid environment, such as in vivo, it is subjected to ultrasonic energy to partially degrade the polymer thereby to release the composition or molecule encapsulated by the polymer. It is believed that main polymer chain rupture in the case of biodegradable polymers is thought to be induced by shock waves created through the cavitation which are assumed to cause a rapid compression with subsequent expansion of the surrounding liquid or solid. Apart from the action of shock waves, the collapse of cavitation bubbles is thought to create pronounced perturbation in the surrounding liquid which can possible induce other chemical effects as well. The agitation may increase the accessibility of liquid molecules, eg water, to the polymer. In the case of nondegradable polymers, cavitation may enhance the diffusion process of molecules out of these polymers.

The acoustic energy and the extent of modulation can readily be moditored over wide range of frequencies and intensities. This of course will depend upon the particular polymeric matrix utilized in the composition which is encapsulated by the polymeric matrix. In order to assure safety of the in vivo implant to the patient, a particular polymeric matrix-composition system can be easily tested in a liquid medium which approaches that of an invivo environment and observing the rate of release of the encapsulated composition under the influence of ultrasonic energy. Representative suitable ultrasonic frequencies are between about 20 KHz and about 1000 KHz, usually between about 50 KHz and about 200 KHz while the intensities can range between about 1 watt and about 30 watts, generally between about 5 w and about 20 w. The times at which the polymer matric-composition system are exposed to ultrasonic energy obviously can vary over a wide range depending upon the environment of use. Generally suitable times are between about seconds and about hours, usually between about about 1 minute and about 2 hours.

It has been found that in accordance with this invention the release rates of the molecules, eg biologically active substances from a polymeric matrix can be repeatedly modulated at will from a position external to the environment of use by ultrasonic energy. Upon subjecting a polymeric matrix to ultrasonic energy, increased release rates of more than about 200 fold can be routinely obtained as compared to the best that has been done with the above-described magnetic ststem of thirty fold. In addition, diagnostic ultrasound techniques are a routine technique which is safe, painless and riskless in any medical applications. In neurology, for example, ultrasonic testing is used to detect brain tumors, clots, and identify subdural hematomas. The power levels employed in ultrasonic testing are very low and on the basis of extensive clinical and experimental data, these tests are considered quite safe for the patient. Accordingly, the process utilized in the present invention also is quite safe.

The following examples illustrate the present invention and are not intended to limit the same.

Bioerodible polyanhydrides were used as the drug carrier matrix. The poly bis(p-carboxy phenoxy) alkane anhydrides having the strucural formula in equation 1 were utilized.

Equation 1

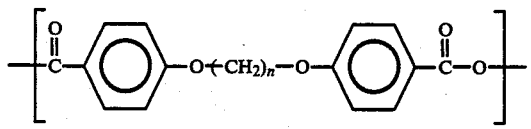

Drug incorporation matrices were formulated either by compression or injection molding a mixture of finely ground sieved (90-150 mm) polymer and drug were pressed into circular discs in a Carver test cylinder outfit at 30 Kpfi at 5° C. above Tg for ten minutes. Injection molding was performed in an SCI mini max injection molder. A molding temperature of 10° C. above the Tm was used. The polymer drug matrix was extruded once for better mixing before the final molding. The basing agent used for samll p-nitroaniline with loading levels up to 10 percent.

The triggering device was a RAI Research Corporation Ultrasonic Cleaner model 250, which generated an ultrasonic frequency of 75 KH$_z$ in a stainless steel tank of 3.5 inches by 3.5 inches by 2.5 inches filled with water. Drug incorporated polymeric matrices were placed in a jacket vial filled with phosphate buffer, pH 7.4 at 37° C. and were exposed to alternating periods of triggering and non triggering in the ultrasonic controlled bath. (FIG. 1) after each period the sample was transferred to fresh release media. The absorbence of the release media was determined spectrophotometrically at 250 nm for monomer degradation products detection and 381 nm for the small p-nitroanilin.

Figure 2:
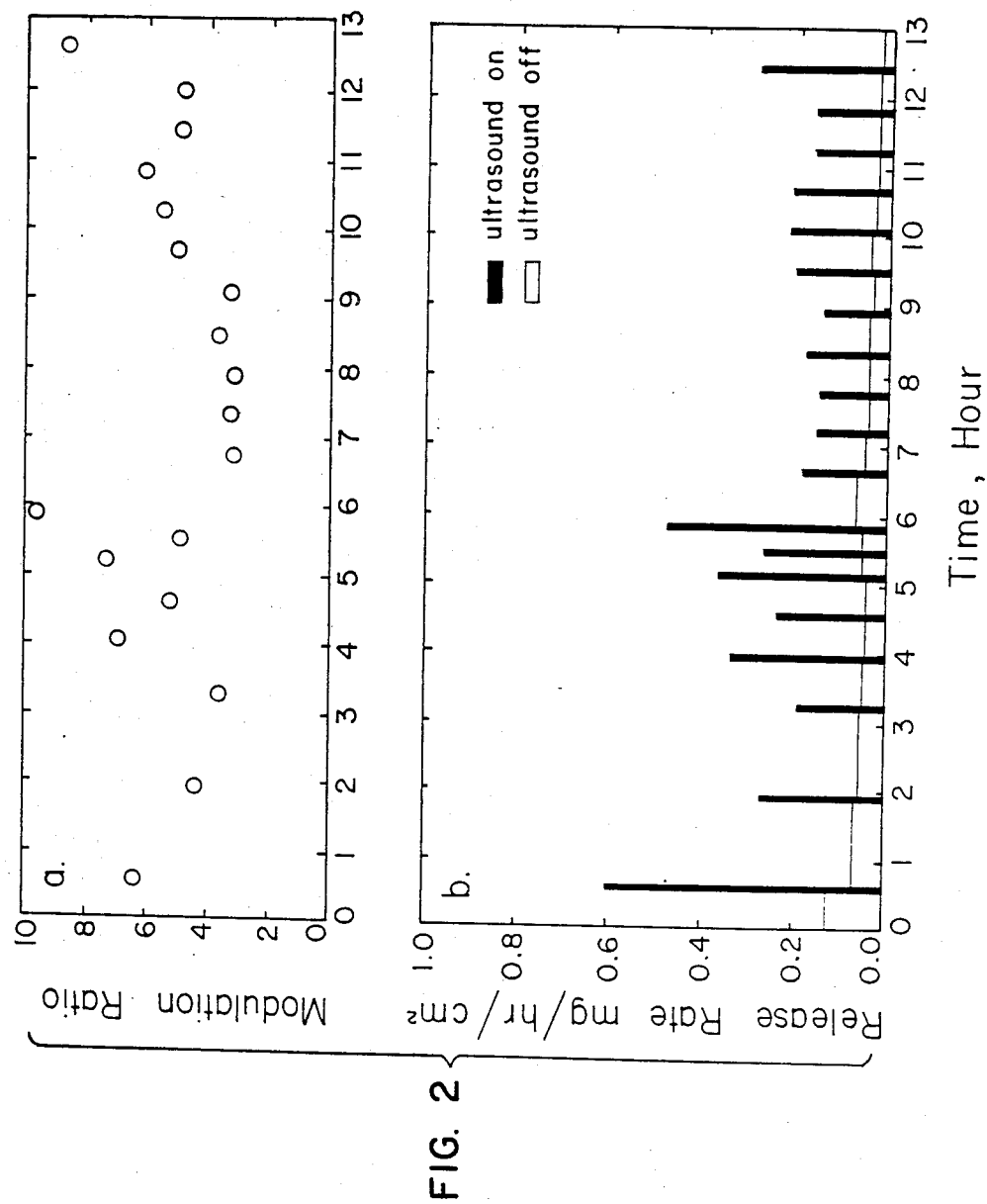
FIGS. 2a and 2b respectively are graphs illustrating the rate of release for drugs and the individual modulation ratios over time from molded poly matrices with and without the use of 75 KH$_z$ ultrasonic energy.
Figure 3:
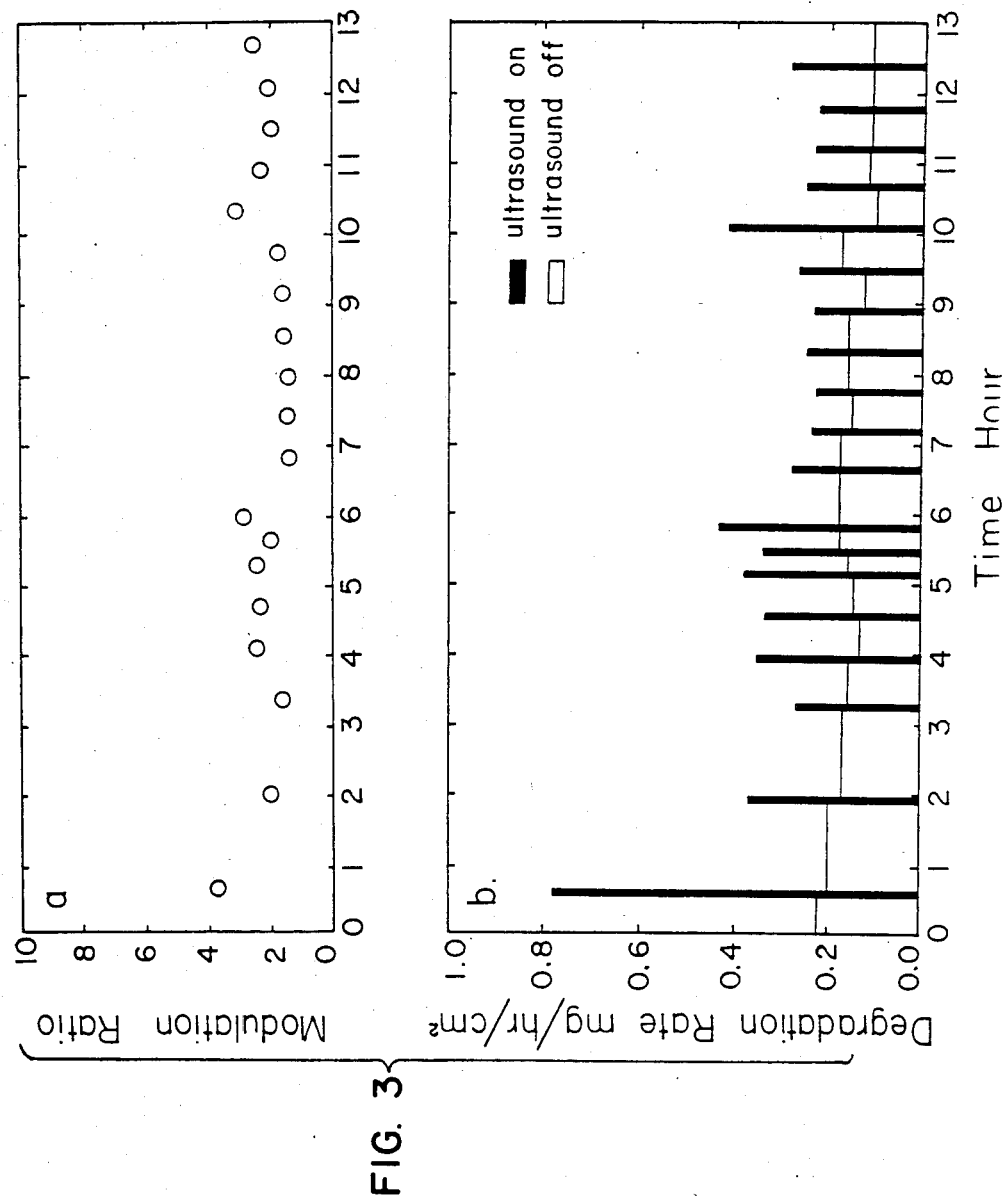
FIGS. 3a and 3b respectively are graphs illustrating the degradation rates for molded poly matrices and individual modulation ratios over time with and without the use of 75 KH$_z$ ultrasonic energy.

The effects of the ultrasonic triggering on degradation and release rates of injection molded poly bis(p-carboxy phenoxy) methane PCPM samples are shown in FIGS. 2b and 3b. As can be seen there is a good correlation between the release rates and degradation, which suggests that the increase in release rates during the triggering is mainly due to enhanced erosion of the polymeric matrix. However, modulation has also been observed, although to a somewhat lesser extent, when molecules such as bovine serum albumin or insulin were incorporated into nondegradable polymers such as ethylene vinyl acetate (40 wt %). using published techniques, (Langer R., Meth. Enzymol.) 73,57, 1981) and ultrasound was applied as above. The extent of modulation is more clearly expressed as the ratio of the rate of release (or degradation) in a given period of ultrasound exposure compared to the actual rates immediately preceeding and following exposure (FIGS. 2a and 3a). This study demonstrates that in vitro release of a drug from a polymeric system can be increased on demand by ultrasound.

We claim:

1. A process for delivering a biologically active substance on demand comprising the steps of:
   combining a biologically active substance with a biocompatible polymeric composition as an admixture;
   forming said admixture into a shaped, solid polymeric matrix;
   implanting said solid polymeic matrix in-vivo at a preselected site such that said solid implanted matrix is in a liquid environment; and
   exposing said implanted solid polymeric matrix to ultrasonic energy for a predetermined time to effect cavitation of said solid polymeric matrix by rapid compression with subsequent expansion of liquid or solid surrounding said solid polymeric matrix thereby to control the rate of release of said biologically active substance from said matrix over a specific time period wherein the rate of release is changed during said time period.

2. The process of claim 1 wherein said exposure to ultrasonic energy degrades said polymeric matrix.

3. The process of claim 1 wherein said polymeric matrix is a polyanhydride.

4. The process of claim 1 polymeric matrix is a copolymer of ethylene and vinyl acetate.

5. The process of claim 1 wherein said biologically active substance is a drug.

6. The process of claim 1 wherein said biologically active composition is insulin.

* * * * *